United States Patent
Katayama et al.

(10) Patent No.: US 8,932,626 B2
(45) Date of Patent: Jan. 13, 2015

(54) FELBINAC-CONTAINING TRANSDERMALLY ABSORBABLE PREPARATION

(75) Inventors: Akiko Katayama, Higashikagawa (JP); Katsuyuki Inoo, Higashikagawa (JP)

(73) Assignee: Teikoku Seiyaku Co., Ltd., Higashikagawa-shi (JP)

( * ) Notice: Subject to any disclaimer, the term of this patent is extended or adjusted under 35 U.S.C. 154(b) by 0 days.

(21) Appl. No.: 13/516,008

(22) PCT Filed: Dec. 14, 2010

(86) PCT No.: PCT/JP2010/072453
§ 371 (c)(1),
(2), (4) Date: Aug. 16, 2012

(87) PCT Pub. No.: WO2011/074566
PCT Pub. Date: Jun. 23, 2011

(65) Prior Publication Data
US 2013/0035391 A1 Feb. 7, 2013

(30) Foreign Application Priority Data
Dec. 15, 2009 (JP) .................. 2009-284325

(51) Int. Cl.
*A61K 31/19* (2006.01)
*A61K 31/167* (2006.01)
*A61K 9/70* (2006.01)
*A61K 31/192* (2006.01)

(52) U.S. Cl.
CPC ............. *A61K 31/167* (2013.01); *A61K 31/192* (2013.01); *A61K 9/7053* (2013.01)
USPC ........................... 424/449; 514/555; 514/579

(58) Field of Classification Search
USPC .................................. 424/449; 514/555, 579
See application file for complete search history.

(56) References Cited

U.S. PATENT DOCUMENTS

| | | | |
|---|---|---|---|
| 7,018,647 B1 * | 3/2006 | Yamasaki et al. | 424/449 |
| 2002/0031542 A1 * | 3/2002 | Takada et al. | 424/447 |

* cited by examiner

*Primary Examiner* — Sean Basquill
*Assistant Examiner* — Kauser M Akhoon
(74) *Attorney, Agent, or Firm* — Crowell & Moring LLP

(57) ABSTRACT

An adhesive patch is a felbinac-containing transdermally absorbable preparation substantially free of a solubilizer for felbinac in a final preparation but still having high releasing of felbinac. The adhesive patch in which lidocaine and felbinac are formulated has the releasing of felbinac without losing the releasing of lidocaine. The felbinac-containing transdermally absorbable adhesive patch contains felbinac as an active component and lidocaine or a pharmaceutically acceptable salt thereof as an absorption promoter. In particular, the content of felbinac is from 0.1% to 10% by weight to the total weight of the drug-containing plaster and the content of lidocaine or the pharmaceutically acceptable salt thereof is from 0.01% to 20% by weight to the total weight of the drug-containing plaster.

3 Claims, 3 Drawing Sheets

FELBINAC-CONTAINING TRANSDERMALLY ABSORBABLE PREPARATION

TECHNICAL FIELD

The present invention relates to a transdermally absorbable preparation, and more particularly, to an adhesive patch containing felbinac, a non-steroidal anti-inflammatory analgesic, as a medicinal component and lidocaine or a pharmaceutically acceptable salt thereof being a local anesthetic and as an absorption promoter to felbinac.

BACKGROUND ART

Felbinac, which is a non-steroidal anti-inflammatory analgesic, is an active metabolite of fenbufen and a drug having high anti-inflammatory and analgesic activity. Felbinac has been transdermally administered to avoid systemic side effects and available as external preparations such as a gel, a liquid, a cataplasm, and a plaster.

Felbinac itself has very low solubility in various solvents. Thus, a variety of solubilizers have been conventionally used in such external preparations to enhance the transdermal absorption of felbinac.

For example, Patent Document 1 has proposed a felbinac-containing plaster which contains crotamiton having high solubilizing ability for felbinac as an essential component. Also, Patent Document 2 has proposed a plaster in which N-methyl-2-pyrrolidone and polyethylene glycol are formulated as the solubilizers. Many of such solubilizers, however, have caused irritation to the skin. Moreover, when such liquid components are formulated in an adhesive patch, a change of the physical properties of the adhesive patch may be caused over time by the bleed-out to the surface (the exudation to the surface) of the adhesive patch.

In addition, Patent Document 3 has proposed a plaster free of crotamiton and containing a styrene-isoprene-styrene block copolymer, a rosin resin, a plasticizer, 1-menthol, and felbinac. This plaster is an adhesive patch in which felbinac is uniformly dispersed in a semi-molten state in the adhesive layer, i.e., in a state wherein felbinac is present in a molten state and in a fine crystalline state simultaneously. The drug permeability however was not sufficient because part of felbinac was present in a crystalline state.

Further, a combination preparation in which a non-steroidal anti-inflammatory analgesic and a local anesthetic are formulated has been studied wherein the preparation has both an anti-inflammatory activity of the non-steroidal anti-inflammatory analgesic and an analgesic activity of the local anesthetic.

For example, Patent Document 4 and Patent Document 5 have proposed a cataplasm in which a non-steroidal anti-inflammatory analgesic such as indomethacin, felbinac, diclofenac sodium and loxoprofen sodium and a local anesthetic such as lidocaine, benzocaine and dibucaine are formulated. Also, Patent Document 6 and Patent Document 7 have proposed a tape in which a non-steroidal anti-inflammatory analgesic and a local anesthetic are formulated respectively.

In general, however, many local anesthetics are basic drugs, while many non-steroidal anti-inflammatory analgesics to be formulated together are acidic drugs including indomethacin and ketoprofen. Accordingly, when these both drugs were simultaneously formulated in the adhesive patch, these formed salts and inhibited the drug releasing of each other, thereby failing to obtain a desired medicinal effect.

PRIOR ART DOCUMENTS

Patent Documents

Patent Document 1: Japanese Patent Application Laid-Open No. Hei. 4-321624
Patent Document 2: Japanese Patent Application Laid-Open No. 2001-342130
Patent Document 3: Japanese Patent Application Laid-Open No. 2003-286162
Patent Document 4: Japanese Patent Application Laid-Open No. 2002-128699
Patent Document 5: International Publication No. WO 01/047559
Patent Document 6: Japanese Patent Application Laid-Open No. 2005-145931
Patent Document 7: Japanese Patent Application Laid-Open No. 2005-145932

Thus, as for the adhesive patch in which a non-steroidal anti-inflammatory analgesic and a local anesthetic as a transdermal absorption promoter are formulated, it has been desired to develop the transdermally absorbable preparation which achieves high anti-inflammatory and analgesic effects without inhibiting drug releasing of each other.

Under such circumstances, as for felbinac among non-steroidal anti-inflammatory analgesics, the present inventors have intensively studied development of the transdermally absorbable preparation, which achieves high anti-inflammatory and analgesic effects without inhibiting the drug releasing of each other, by formulating felbinac with a local anesthetic as a transdermal absorption promoter.

As a result, when lidocaine was selected as the absorption promoter and formulated together with the non-steroidal anti-inflammatory analgesic felbinac in an adhesive patch base, it was found that a uniform drug-containing plaster was obtained even substantially free of the solubilizer for felbinac to provide a felbinac-containing transdermally absorbable preparation having high releasing of main drugs while the transdermally absorbable preparation had excellent analgesic and anti-inflammatory activity without losing the transdermal absorption of lidocaine as the local anesthetic, thereby completing the present invention.

SUMMARY OF THE INVENTION

Problems to be Solved by the Invention

Thus, it is a first object of the present invention to provide a felbinac-containing transdermally absorbable preparation substantially free of a solubilizer for felbinac in a final preparation but still having high releasing of felbinac to solve the above-mentioned conventional problems.

Further, it is a second object of the present invention to provide an adhesive patch in which a local anesthetic and felbinac, which is the non-steroidal anti-inflammatory analgesic, are formulated, wherein the adhesive patch has excellent releasing of the non-steroidal anti-inflammatory analgesic without losing the releasing of the local anesthetic.

Means for Solving the Problem

A basic aspect of the present invention to solve such problems is a felbinac-containing transdermally absorbable adhesive patch, which contains felbinac as an active component and lidocaine or a pharmaceutically acceptable salt thereof as an absorption promoter.

Specifically, the present invention is the felbinac-containing transdermally absorbable adhesive patch wherein the content of felbinac is from 0.1% to 10% by weight to the total weight of the drug-containing plaster base material and the content of lidocaine or the pharmaceutically acceptable salt thereof is from 0.01% to 20% by weight to the total weight of the drug-containing plaster base material.

Especially, the present invention is the felbinac-containing transdermally absorbable adhesive patch wherein an adhesive patch base is a rubber polymer and the rubber polymer is a styrene-isoprene-styrene block copolymer.

Also, the present invention is, from another point of view, each felbinac-containing transdermally absorbable preparation described above which is substantially free of a solubilizer for felbinac in the final preparation.

Effects of the Invention

The present invention provides the felbinac-containing transdermally absorbable adhesive patch, which contains felbinac as the anti-inflammatory analgesic component and lidocaine or the pharmaceutically acceptable salt thereof as the absorption promoter.

Particularly, in the present invention, by combining with lidocaine or the pharmaceutically acceptable salt thereof as the absorption promoter for felbinac in the adhesive patch base, felbinac can be uniformly contained in a plaster composition without substantially formulating a solubilizer for felbinac. Accordingly, the present invention provides the transdermally absorbable preparation having high releasing of felbinac and excellent analgesic and anti-inflammatory effects at the same time without the transdermal absorption of lidocaine as the local anesthetic being decreased.

As found in the results of Test Examples described below, the absorption promoting effect caused by formulating lidocaine is specific for felbinac among anti-inflammatory analgesics. Thus, the present invention has a great medical effect in that the adhesive patch of the transdermally absorbable preparation containing clinically extremely useful felbinac can be provided.

EMBODIMENTS FOR CARRYING OUT THE INVENTION

Figure 1:
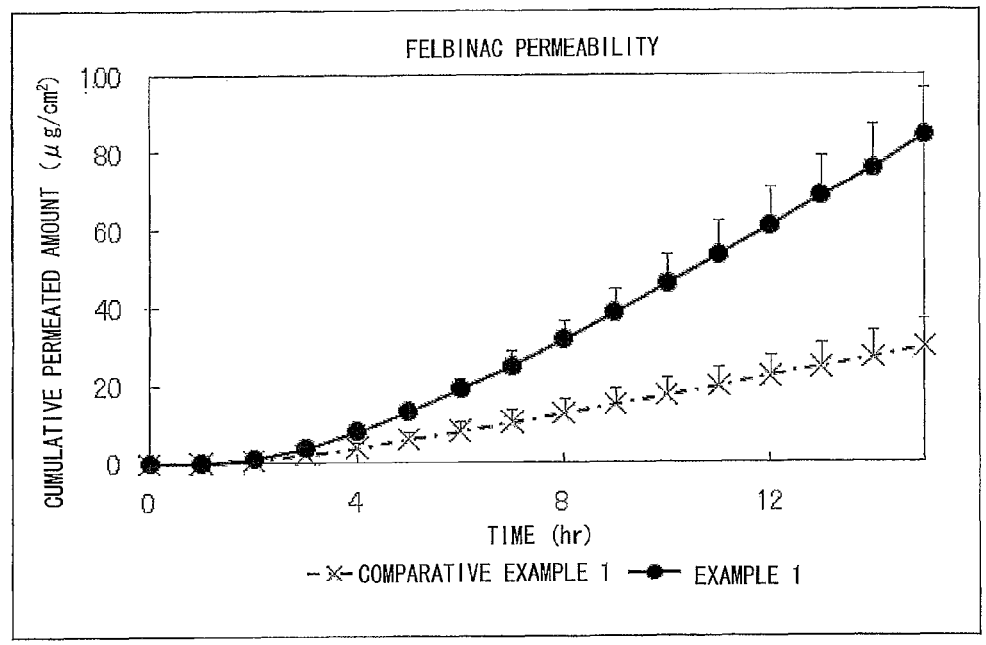
FIG. 1 is a graph showing the result of in vitro rat skin permeability test for felbinac based on Comparative Study (1) of Test Example 1.

The basic aspect of the present invention, as described above, is the felbinac-containing transdermally absorbable adhesive patch, which contains felbinac as an anti-inflammatory analgesic medicinal component and lidocaine or a pharmaceutically acceptable salt thereof as an absorption promoter.

The formulated amount of the active component felbinac in the adhesive patch of the present invention is from 0.1% to 10% by weight and particularly preferably from 0.2% to 5% by weight to the total weight of the drug-containing base material.

When the formulated amount of felbinac is less than 0.1% by weight, the medicinal effect of felbinac may not be sufficient. More than 10% by weight of felbinac formulated is also not preferable because irritation to the skin may be caused or the physical properties of the plaster may be lost.

On the other hand, in the present invention, lidocaine to be formulated with felbinac not only shows an analgesic activity as the local anesthetic by itself but also acts as the absorption promoter for felbinac in the present invention.

In this case, the formulated amount of lidocaine is preferably from 0.01% to 20% by weight and more preferably from 0.1% to 10% by weight to the total weight of the drug-containing base material.

The formulated amount of less than 0.01% by weight of lidocaine cannot enhance the skin permeability of felbinac sufficiently. On the other hand, more than 20% by weight of lidocaine is also not preferable because not only the effect of lidocaine formulated cannot be expected but also irritation to the skin may be caused or the physical properties of the plaster may be lost.

In another feature of the present invention, by formulating lidocaine with felbinac in the adhesive patch base material, the felbinac-containing transdermally absorbable adhesive patch substantially free of the solubilizer for felbinac in the final preparation is provided.

In the present invention, "substantially free of the solubilizer" means that, although a small amount of used solvent is unavoidably remained in the preparation of interest due to the manufacturing process of the preparation, the solubilizer is not contained as long as the amount of the solvent is sufficiently small to have little effect on the transdermal absorption of the final preparation.

In other words, the case in which the amount of the residual solvent is sufficiently small to have little effect on the drug releasing in the final preparation can be regarded as "substantially free of the solubilizer".

The plaster composition used in the adhesive patch base material provided by the present invention can be prepared by mixing felbinac and lidocaine with the adhesive patch base component.

Such an adhesive patch base component is not particularly limited as long as it can become the base of an adhesive layer which is the plaster composition, and hydrophobic polymers such as a rubber polymer, an acrylic polymer and a silicon polymer are preferably used.

Examples of the rubber polymer may include a styrene-isoprene-styrene block copolymer (hereinafter, referred to as SIS), polyisobutylene (hereinafter, referred to as PIB), a styrene-butadiene-styrene block copolymer (hereinafter, referred to as SBS), a styrene-butadiene rubber (hereinafter, referred to as SBR), an isoprene rubber and the like. Among them, SIS is particularly preferred.

Also, the acrylic polymer is not particularly limited as long as one of (meth)acrylic acid derivatives represented by 2-ethylhexyl acrylate, methyl acrylate, butyl acrylate, hydroxyethyl acrylate, 2-ethylhexyl methacrylate and the like is contained and copolymerized. For example, the adhesives listed in Japanese Pharmaceutical Excipients Directory 2007 (edited by International Pharmaceutical Excipients Council Japan) such as the adhesive of an acrylic polymer which contains an acrylic acid/octyl acrylate copolymer, a 2-ethylhexyl acrylate/vinylpyrrolidone copolymer solution, an acrylate-vinyl acetate copolymer, a 2-ethylhexyl acrylate-2-ethylhexyl methacrylate/dodecyl methacrylate copolymer, a methyl acrylate-2-ethylhexyl acrylate copolymer resin emulsion, an acrylic resin alkanol amine solution and the like, DURO-TAK acrylic adhesive series (produced by National Starch and Chemical Company) and Eudragit series (HIGUCHI Inc.) can be used.

Moreover, specific examples of the silicon polymer may include a silicone rubber such as polyorganosiloxane.

Such hydrophobic polymers may be used in mixture of two or more. The formulated amount of such polymers based on the mass of the total composition is from 5% to 80% by weight, preferably from 10% to 70% by weight and more preferably from 10% to 50% by weight in consideration of the formation of the adhesive layer and sufficient drug permeability.

The adhesive composition in the adhesive patch which is the transdermally absorbable preparation provided by the present invention may contain a plasticizer. Examples of the plasticizer to be used may include a petroleum-based oil (for example, a paraffin-based process oil such as a liquid paraffin, a naphthene-based process oil, an aromatic process oil and the like), squalane, squalene, a vegetable oil (for example, an olive oil, a camellia oil, a tall oil, a peanut oil, a castor oil and the like), a silicone oil, dibasic acid ester (for example, dibutyl phthalate, dioctyl phthalate and the like), a liquid rubber (for example, polybutene, a liquid isoprene rubber and the like), liquid fatty acid esters (for example, isopropyl myristate, hexyl laurate, diethyl sebacate, diisopropyl sebacate and the like). A liquid paraffin is particularly preferred.

Such components may be used in mixture of two or more. The formulated amount of such plasticizers based on the total composition of the adhesive layer is from 1% to 70% by weight, preferably from 10% to 60% by weight and more preferably from 10% to 50% by weight in total in consideration of the maintaining of enough cohesion as the adhesive patch.

In the adhesive layer of the present invention, it is desirable to formulate a tackifier resin to adjust the adhesion of the preparation. Examples of the tackifier resin which can be used may include rosin derivatives (for example, rosin, rosin glycerin ester, hydrogenated rosin, hydrogenated rosin glycerin ester, rosin pentaerythritol ester and the like), an alicyclic saturated hydrocarbon resin (for example, Alcon P100, Arakawa Chemical Industries Ltd.), an aliphatic hydrocarbon resin (for example, Quinton B170, Nippon Zeon Co., Ltd.), a terpene resin (for example, Clearon P-125, Yasuhara Chemical Co., Ltd.), a maleic acid resin and the like.

The formulated amount of such a tackifier resin based on the total composition of the adhesive composition can be from 5% to 70% by weight, preferably from 5% to 60% by weight and more preferably from 10% to 50% by weight in consideration of enough adhesion as the adhesive preparation and irritation to the skin upon being peeled.

Also, an antioxidant, a filler, a cross-linking agent, a preservative and an ultraviolet absorber can be used if necessary. As the antioxidant, tocopherol and ester derivatives thereof, ascorbic acid, ascorbyl stearate, nordihydroguaiaretic acid, dibutylhydroxy-toluene (hereinafter, referred to as BHT), butylhydroxyanisole and the like are desirable.

As the filler, calcium carbonate, magnesium carbonate, silicate (for example, aluminum silicate, magnesium silicate and the like), silicic acid, barium sulfate, calcium sulfate, calcium zincate, zinc oxide, titanium oxide and the like are desirable.

As the cross-linking agent, a thermosetting resin such as an amino resin, a phenolic resin, an epoxy resin, an alkyd resin and unsaturated polyester; an isocyanate compound; a blocked isocyanate compound; an organic cross-linking agent; and an inorganic cross-linking agent such as a metal and a metal compound are desirable.

As the preservative, paraben such as ethyl parahydroxybenzoate, propyl parahydroxybenzoate and butyl parahydroxybenzoate is desirable.

As the ultraviolet absorber, p-aminobenzoic acid derivatives, anthranilic acid derivatives, salicylic acid derivatives, amino acid compounds, dioxane derivatives, coumarin derivatives, imidazoline derivatives, pyrimidine derivatives and the like are desirable.

Such an antioxidant, a filler, a cross-linking agent, a preservative and an ultraviolet absorber can be formulated in 10% by weight or less, preferably 5% by weight or less and more preferably 2% by weight or less based on the mass of the total composition of the adhesive layer of the preparation.

The adhesive patch, which is the transdermally absorbable preparation of the present invention having the composition described above, can be produced by any methods.

Examples of the methods include generally called a hot melt method and a solvent method. In the hot melt method, the adhesive patch can be obtained by thermally melting the drug-containing base component, coating it on a release film or a support, and laminating the base component to a support or a release film. In the solvent method, the adhesive patch can be obtained by dissolving the drug-containing base component in an organic solvent such as toluene, hexane, ethyl acetate or N-methyl-2-pyrrolidone, spreading and coating it on a release film or a support, removing the solvent by drying, and laminating the base component to a support or a release film.

In the adhesive patch, which is the external transdermal preparation provided by the present invention, the thickness of the adhesive layer is not particularly limited, but generally 500 μm or less and preferably from 20 μm to 300 μm.

As the support of the adhesive patch, which is the transdermally absorbable preparation of the present invention, an elastic or a non-elastic support can be used. For example, it is selected from fabrics, nonwoven fabrics, polyurethane, polyester, polyvinyl acetate, polyvinylidene chloride, polyethylene, polyethylene terephthalate (hereinafter, referred to as PET), an aluminum sheet and the like, or the composite material thereof.

The release film is not particularly limited as long as it protects the adhesive layer without the main drug components being decomposed until the adhesive patch, which is the transdermally absorbable preparation, is applied to the skin and it is silicon coated to be easily peeled. Specific examples of the release film include a silicon coated polyethylene film, PET film and polypropylene film.

EXAMPLE

Hereinafter, the present invention will be described more specifically by illustrating Examples, Preparation Examples and Test Examples of the present invention, but the present invention is not limited to these Examples and Preparation Examples and various modifications thereof can be made without departing from the technical idea of the present invention.

Here, in the following description, all of "%" mean "% by weight" unless otherwise specified.

Example 1

Felbinac/Lidocaine Formulated Preparation

The external adhesive patch in which both felbinac and lidocaine were formulated was prepared.

(Components)

|  |  |
|---|---|
| SIS | 16% |
| Liquid paraffin | 28% |
| BHT | 1% |
| Hydrogenated rosin glycerin ester | 40% |
| Lidocaine | 10% |
| Felbinac | 5% |
| Total | 100% |

(Process)

Felbinac was dissolved in advance in N-methyl-2-pyrrolidone and lidocaine was dissolved in toluene. They were mixed with other base components, which were already dissolved in toluene. The mixture was coated on the release film, and subsequently toluene and N-methyl-2-pyrrolidone were removed by drying. The obtained product was laminated with the PET film support to provide a desirable transdermally absorbable preparation (the thickness of the adhesive layer was 100 μm).

Comparative Example 1

Felbinac Formulated Preparation

The external adhesive patch in which only felbinac was formulated was prepared as Comparative Example 1.
(Components)

|  |  |
|---|---|
| SIS | 16% |
| Liquid paraffin | 38% |
| BHT | 1% |
| Hydrogenated rosin glycerin ester | 40% |
| Felbinac | 5% |
| Total | 100% |

(Process)

Felbinac was dissolved in advance in N-methyl-2-pyrrolidone, and the solution was mixed with other base components which were already dissolved in toluene. The mixture was coated on the release film, and subsequently toluene and N-methyl-2-pyrrolidone were removed by drying. The obtained product was laminated with the PET film support to provide a desirable transdermally absorbable preparation (the thickness of the adhesive layer was 100 μm).

Comparative Example 2

Lidocaine Formulated Preparation

The external adhesive patch in which only lidocaine was formulated was prepared as Comparative Example 2.
(Components)

|  |  |
|---|---|
| SIS | 16% |
| Liquid paraffin | 33% |
| BHT | 1% |
| Hydrogenated rosin glycerin ester | 40% |
| Lidocaine | 10% |
| Total | 100% |

(Process)

Lidocaine was dissolved in advance in toluene, and the solution was mixed with other base components which were already dissolved in toluene. The mixture was coated on the release film, and subsequently toluene was removed by drying. The obtained product was laminated with the PET film support to provide a desirable transdermally absorbable preparation (the thickness of the adhesive layer was 100 μm).

Comparative Example 3

Ketoprofen Formulated Preparation

The external adhesive patch in which only ketoprofen, which is another anti-inflammatory analgesic was formulated was prepared as Comparative Example 3.
(Components)

|  |  |
|---|---|
| SIS | 16% |
| Liquid paraffin | 38% |
| BHT | 1% |
| Hydrogenated rosin glycerin ester | 40% |
| Ketoprofen | 5% |
| Total | 100% |

(Process)

Ketoprofen was dissolved in advance in N-methyl-2-pyrrolidone, and the solution was mixed with other base components which were already dissolved in toluene. The mixture was coated on the release film, and subsequently toluene and N-methyl-2-pyrrolidone were removed by drying. The obtained product was laminated with the PET film support to provide a desirable transdermally absorbable preparation (the thickness of the adhesive layer was 100 μm).

Comparative Example 4

Ketoprofen/Lidocaine Formulated Preparation

The external adhesive patch in which ketoprofen which is another anti-inflammatory analgesic was used in combination with lidocaine was prepared as Comparative Example 4.
(Components)

|  |  |
|---|---|
| SIS | 16% |
| Liquid paraffin | 28% |
| BHT | 1% |
| Hydrogenated rosin glycerin ester | 40% |
| Lidocaine | 10% |
| Ketoprofen | 5% |
| Total | 100% |

(Process)

Ketoprofen was dissolved in advance in N-methyl-2-pyrrolidone and lidocaine was dissolved in toluene. They were mixed with other base components, which were already dissolved in toluene. The mixture was coated on the release film, and subsequently toluene and N-methyl-2-pyrrolidone were removed by drying. The obtained product was laminated with the PET film support to provide a desirable transdermally absorbable preparation (the thickness of the adhesive layer was 100 μm).

Comparative Example 3

Indomethacin Formulated Preparation

The external adhesive patch in which only indomethacin, which is another anti-inflammatory analgesic was formulated, was prepared as Comparative Example 5.

(Components)

| | |
|---|---|
| SIS | 16% |
| Liquid paraffin | 38% |
| BHT | 1% |
| Hydrogenated rosin glycerin ester | 40% |
| Indomethacin | 5% |
| Total | 100% |

(Process)

Indomethacin was dissolved in advance in N-methyl-2-pyrrolidone, and the solution was mixed with other base components which were already dissolved in toluene. The mixture was coated on the release film, and subsequently toluene and N-methyl-2-pyrrolidone were removed by drying. The obtained product was laminated with the PET film support to provide a desirable transdermally absorbable preparation (the thickness of the adhesive layer was 100 µm).

Comparative Example 6

Indomethacin/Lidocaine Formulated Preparation

The external adhesive patch in which indomethacin which is another anti-inflammatory analgesic was used in combination with lidocaine was prepared as Comparative Example 5.

(Components)

| | |
|---|---|
| SIS | 16% |
| Liquid paraffin | 28% |
| BHT | 1% |
| Hydrogenated rosin glycerin ester | 40% |
| Lidocaine | 10% |
| Indomethacin | 5% |
| Total | 100% |

(Process)

Indomethacin was dissolved in advance in N-methyl-2-pyrrolidone and lidocaine was dissolved in toluene. They were mixed with other base components, which were already dissolved in toluene. The mixture was coated on the release film, and subsequently toluene and N-methyl-2-pyrrolidone were removed by drying. The obtained product was laminated with the PET film support to provide a desirable transdermally absorbable preparation (the thickness of the adhesive layer was 100 µm).

Test Example 1

Rat Skin Permeability Test

In vitro skin permeability test was carried out with the skin excised from the male rat (Wister strain, 8 week old) for each external preparation prepared in the above Example 1 and Comparative Examples 1 to 6 to study the specificity of the releasing of felbinac and lidocaine in the external adhesive patch of the present invention in which both felbinac and lidocaine were formulated in accordance with Comparative Studies (1) to (3) described below.

[Method]

The rat abdominal skin was exfoliated, the dermis side of the skin was directed to a side of a receptor layer, and its inside was filled with phosphate buffered saline. Water kept at 37° C. was circulated in a water jacket. Each test preparation prepared in Example 1 and Comparative Examples 1 to 6 was stamped out in a circle (1.77 cm$^2$) and attached to the excised skin. The receptor solution was sampled over time to measure the permeated amount of each drug (lidocaine, felbinac, ketoprofen, and indomethacin) by high performance liquid chromatography.

[Comparative Study]

(1) Comparison of the releasing of felbinac and/or lidocaine by comparing the preparation of Example 1 in which both felbinac and lidocaine are formulated in the external adhesive patch of the present invention, the preparation of Comparative Example 1 in which only felbinac is formulated, and the preparation of Comparative Example 2 in which only lidocaine is formulated.

(2) For ketoprofen which is another anti-inflammatory analgesic, comparison of the releasing of ketoprofen and/or lidocaine by comparing the preparation of Comparative Example 3 in which only ketoprofen is formulated, the preparation of Comparative Example 4 in which both ketoprofen and lidocaine are formulated, and furthermore Comparative Example 2 in which only lidocaine is formulated.

(3) For indomethacin which is another anti-inflammatory analgesic, comparison of the releasing of indomethacin and/or lidocaine by comparing the preparation of Comparative Example 5 in which only indomethacin is formulated, the preparation of Comparative Example 6 in which both indomethacin and lidocaine are formulated, and furthermore Comparative Example 2 in which only lidocaine is formulated.

[Result]

The results are shown in FIGS. 1 to 6.

[Consideration]

Consideration to Comparative Study (1)

Figure 2:
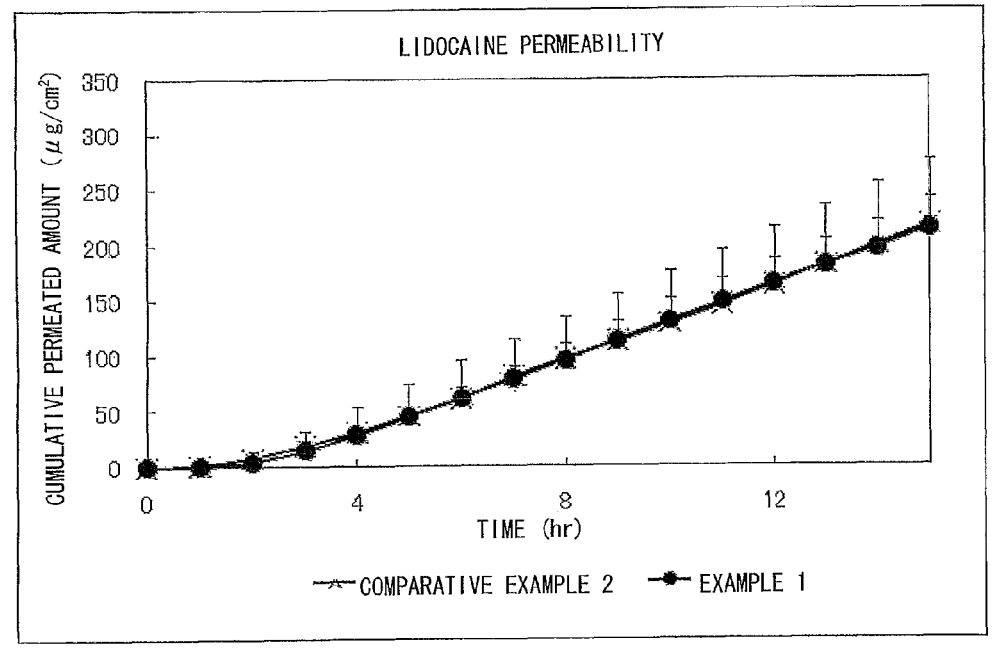
FIG. 2 is a graph showing the result of in vitro rat skin permeability test for lidocaine based on Comparative Study (1) of Test Example 1.

As is apparent in comparison of the results shown in FIGS. 1 and 2, the releasing of felbinac in the external adhesive patch of Example 1 in which both felbinac and lidocaine were formulated was dramatically high compared to the external adhesive patch of Comparative Example 1 in which only felbinac was formulated (FIG. 1).

Also, the releasing of lidocaine in the external adhesive patch of Example 1 in which both felbinac and lidocaine were formulated was almost the same as that of the external adhesive patch of Comparative Example 2 in which only lidocaine was formulated (FIG. 2).

Considering these both results, it is understood that good releasing of lidocaine as the absorption promoter enhances the releasing of felbinac in the external adhesive patch of the present invention in which both felbinac and lidocaine are formulated.

Consideration to Comparative Study (2)

Figure 3:
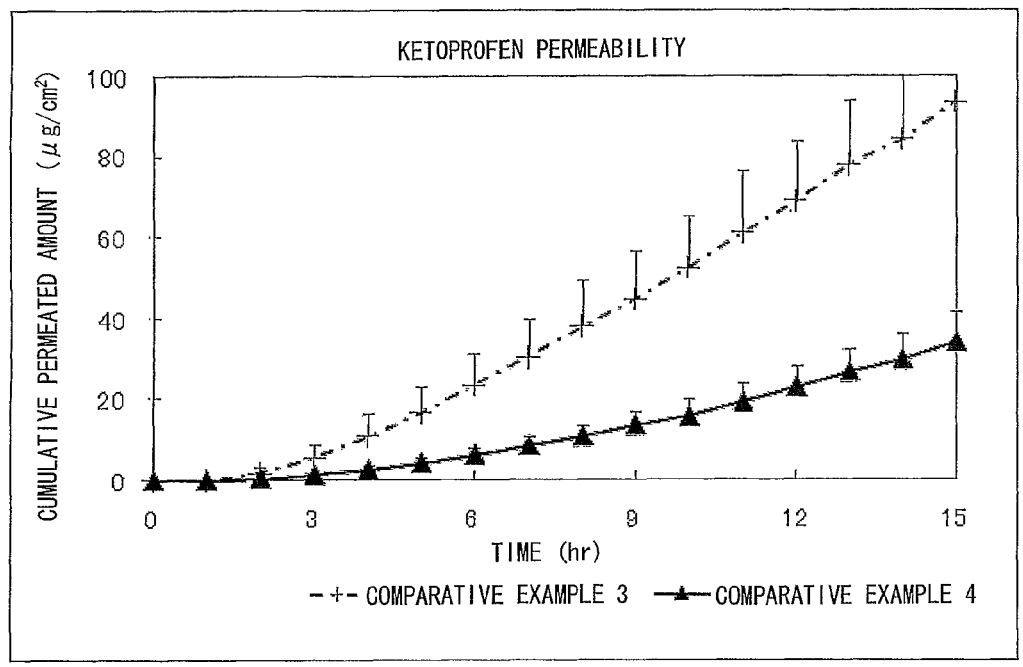
FIG. 3 is a graph showing the result of in vitro rat skin permeability test for ketoprofen of Comparative Example based on Comparative Study (2) of Test Example 1.
Figure 4:
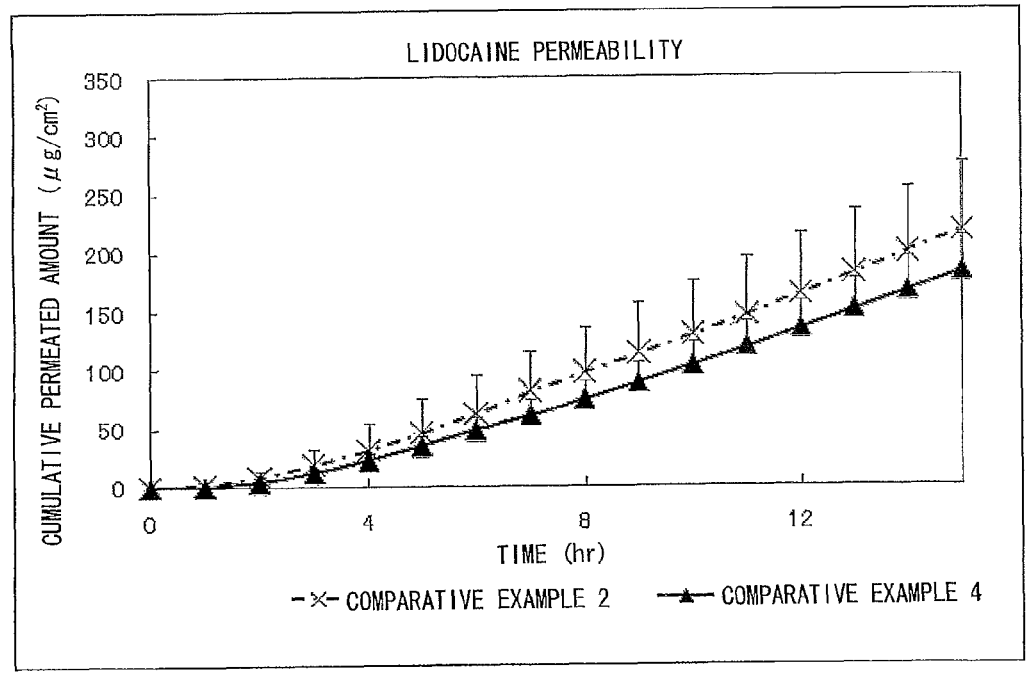
FIG. 4 is a graph showing the result of in vitro rat skin permeability test for lidocaine based on Comparative Study (2) of Test Example 1.
Figure 5:
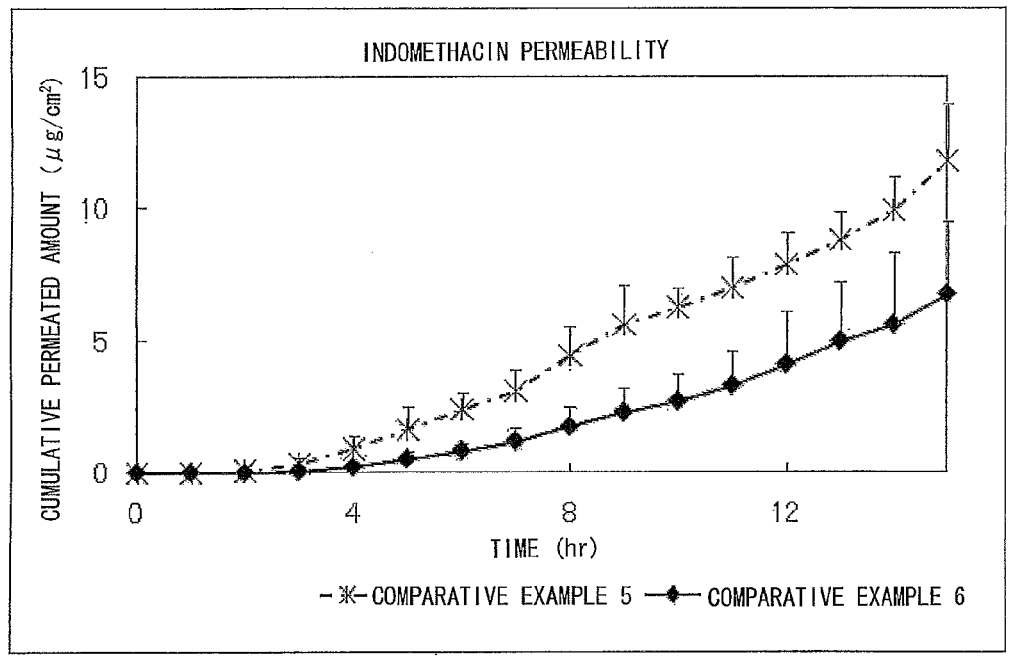
FIG. 5 is a graph showing the result of in vitro rat skin permeability test for indomethacin of Comparative Example based on Comparative Study (3) of Test Example 1.
Figure 6:
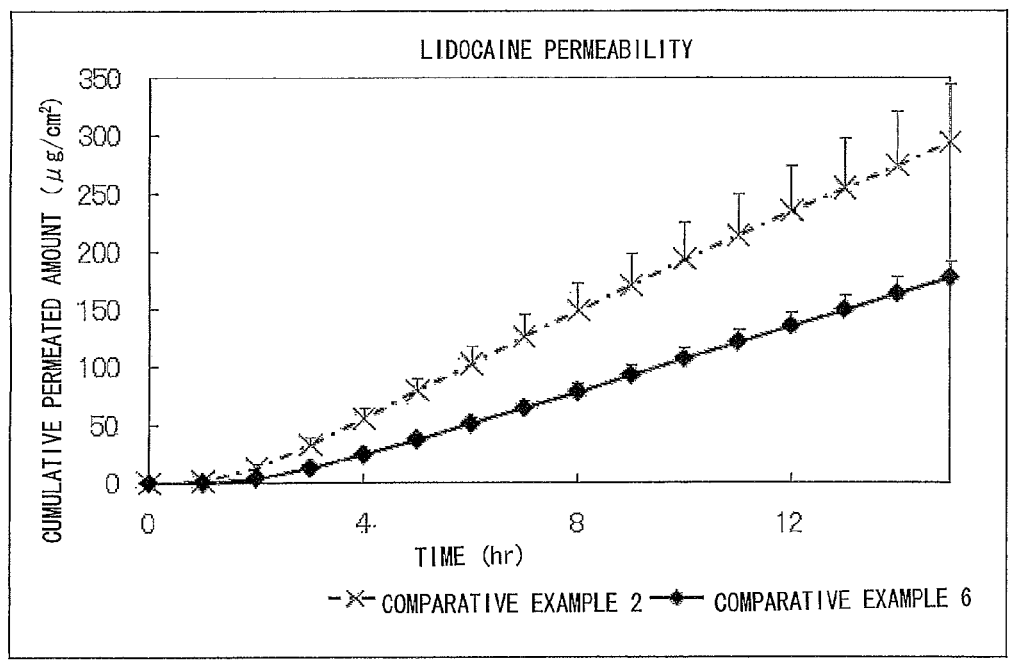
FIG. 6 is a graph showing the result of in vitro rat skin permeability test for lidocaine based on Comparative Study (3) of Test Example 1.

On the other hand, when ketoprofen, which is another anti-inflammatory analgesic, was subjected to the same test to study the releasing of both formulations with or without formulating lidocaine, it was found that lidocaine showed almost the same drug releasing (FIG. 4), but the releasing of ketoprofen was inhibited significantly by formulating lidocaine (FIG. 3).

Consideration to Comparative Study (3)

For indomethacin which is another anti-inflammatory analgesic, the external adhesive patch of Comparative Example 6 in which both indomethacin and lidocaine are formulated had the releasing of both indomethacin and lidocaine inhibited.

According to the results of these Comparative Studies (1) to (3), as for the adhesive patch of the present invention in which lidocaine is formulated as the local anesthetic together with felbinac which is a non-steroidal anti-inflammatory analgesic, it was found that it is the transdermally absorbable preparation in which the releasing of lidocaine is not inhibited significantly and is accompanied by excellent felbinac releasing although it is the preparation in which the basic drug of the local anesthetic and the acidic drug of the non-steroidal anti-inflammatory analgesic are formulated.

Moreover, the releasing effect of the anti-inflammatory analgesic, an active component, obtained by formulating lidocaine is not observed for ketoprofen and indomethacin and is specific only for felbinac among non-steroidal anti-inflammatory analgesics. Therefore, it should be understood that the present invention has extremely excellent specificity.

Preparation Example

Hereinafter, specific Preparation Examples other than the external adhesive patch of the present invention described above in Example 1 are shown below in Table 1. Here, the present invention is not limited thereto.

TABLE 1

| Components | Preparation Example (unit: % by weight) | | | | | |
|---|---|---|---|---|---|---|
| | 1 | 2 | 3 | 4 | 5 | 6 |
| SIS | 16 | 16 | 15 | 19 | 16 | 16 |
| BHT | 1 | 1 | 1 | 1 | 1 | 1 |
| Hydrogenated Rosin Glycerin Ester | 40 | 40 | | | | |
| Terpene Resin | | | | | 40 | |
| Alicyclic Saturated Hydrocarbon Resin | | | 40 | 40 | | 38 |
| Liquid Paraffin | 31 | 21 | 33 | 19.5 | 33 | 33 |
| Lidocaine | 10 | 15 | 10 | 20 | 5 | 8 |
| Felbinac | 2 | 7 | 1 | 0.5 | 5 | 4 |

The thickness of the adhesive layer: 100 μm

INDUSTRIAL APPLICABILITY

As described above, the transdermally absorbable preparation according to the present invention can provide the preparation which shows excellent analgesic effect caused by lidocaine and excellent anti-inflammatory and analgesic effects caused by felbinac.

Particularly, in the present invention, by combining felbinac with lidocaine as the absorption promoter for felbinac in the adhesive patch base, felbinac can be uniformly contained in the plaster composition without substantially formulating a solubilizer for felbinac, and further high releasing of felbinac is kept without losing the releasing of lidocaine. As a result, the present invention can provide the transdermally absorbable preparation which achieves excellent analgesic and anti-inflammatory effects, thereby having a great medical effect.

The invention claimed is:

1. A transdermal adhesive patch comprising an adhesive patch base comprising felbinac as an active component and lidocaine or a pharmaceutically acceptable salt thereof as an absorption promoter; wherein
the adhesive patch base is a styrene-isoprene-styrene block copolymer;
the felbinac is present in an amount of 0.1% to 10% by weight of the total weight of said adhesive patch base; and
the lidocaine or a pharmaceutically acceptable salt thereof is present in an amount of 0.01% to 20% by weight of the total weight of said adhesive patch base.

2. The transdermal adhesive patch according to claim 1, wherein the adhesive patch is substantially free of a solubilizer for felbinac in the final preparation.

3. The transdermal adhesive patch of claim 1 wherein the lidocaine is in an amount of 0.1% to 10% by weight of the total weight of said adhesive patch base.

* * * * *